US00PP30568P2

(12) United States Plant Patent
Egger

(10) Patent No.: US PP30,568 P2
(45) Date of Patent: Jun. 11, 2019

(54) ***HEUCHERA* PLANT NAMED 'TNHEUNEP'**

(50) Latin Name: ***Heuchera* hybrid**
Varietal Denomination: TNHEUNEP

(71) Applicant: Terra Nova Nurseries, Inc., Canby, OR (US)

(72) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 15/932,792

(22) Filed: Apr. 25, 2018

(51) Int. Cl.
*A01H 5/02* (2018.01)
*A01H 6/80* (2018.01)

(52) U.S. Cl.
USPC ..... Plt./440
CPC ..... *A01H 6/80* (2018.05); *A01H 5/02* (2013.01)

(58) Field of Classification Search
USPC ..... Plt./440
CPC ..... A01H 5/02
See application file for complete search history.

(56) References Cited

PUBLICATIONS https://www.greenhousegrower.com/varieties/terra-nova-adds-two-new-heuchera-to-its-northern-exposure-series/; Jan. 18, 2018; 8 pages.*

* cited by examiner

*Primary Examiner* — Kent L Bell
(74) *Attorney, Agent, or Firm* — Klarquist Sparkman, LLP

(57) ABSTRACT

A new and distinct *Heuchera* plant characterized by purple to silver colored leaves, medium size, slightly lobed, geranium-like leaves, light pink flowers, good sun and shade tolerance, a medium-large, mounding habit with excellent crown count, and excellent vigor.

1 Drawing Sheet

Botanical denomination: *Heuchera* hybrid.
Variety designation: 'TNHEUNEP'.

BACKGROUND OF THE INVENTION

The present invention relates to a new and distinct cultivar of *Heuchera* and given the cultivar name of 'TNHEUNEP'. *Heuchera* is in the family Saxifragaceae. *Heuchera* 'TNHEUNEP' originated from a controlled cross using *Heuchera* 'B78-1', a proprietary, unpatented plant as the seed parent, and *Heuchera* 'B88-1', a proprietary, unpatented plant as the pollen parent. These parents are a result of breeding using hardy *Heuchera richardsonii* crossed with proprietary hybrid lines. *Heuchera* 'TNHEUNEP' was bred to be a hardy, large, landscape plant.

The trademark designation for the claimed plant is 'Northern Exposure™ Purple.

Compared to the seed parent, *Heuchera* 'B78-1', the new cultivar has larger leaves and light pink flowers rather than dull yellow.

Compared to the pollen parent, *Heuchera* 'B88-1', the new cultivar has an increased crown count and less of a silver veil.

Compared to *Heuchera* 'Spellbound', U.S. Plant Pat. No. 24,103, the new cultivar has darker purple leaves, less lobed, a larger habit, increased hardiness, higher crown count.

This new *Heuchera* is uniquely distinguished by:

1. purple to silver colored leaves,
2. medium size, slightly lobed, geranium-like leaves,
3. light pink flowers,
4. good sun and shade tolerance, 5. a medium-large, mounding habit with excellent crown count, and
6. excellent vigor.

This new cultivar has been reproduced only by asexual propagation (tip cuttings and tissue culture using growing tips). Each of the progeny exhibits identical characteristics to the original plant. Asexual propagation by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may change with variations in environment without a change in the genotype of the plant.

BRIEF DESCRIPTION OF THE DRAWINGS

FIG. 1 shows a six-month-old plant of *Heuchera* 'TNHEUNEP' growing in a one gallon pot in full sun in August in Canby, Oreg.

DETAILED PLANT DESCRIPTION

The following is a detailed description of the new *Heuchera* cultivar based on observations taken in October of nine-month-old specimens growing in the trial field in Canby, Oreg. Canby is Zone 8 on the USDA Hardiness map. Temperatures range from a high of 95° F. in August to an average of 32° F. in January. Normal rainfall in Canby is 42.8 inches per year. The color descriptions are all based on The *Royal Horticultural Society Colour Chart*, 5$^{th}$ edition, 2007.

Plant:

*Form*.—Basal rosette, herbaceous perennial.

*Hardiness*.—USDA Zone 3 to 9.

*Size*.—69 cm tall from ground to foliage, up to 79 cm tall from top of inflorescences to the ground, 63 cm wide.

*Number of crowns*.—About 10.

*Habit*.—Medium-large, mounding.

*Vigor*.—Excellent.

Leaf:

*Type*.—Simple.

*Arrangement*.—Rosette.

*Shape*.—Broadly ovate to orbicular.

*Number*.—About 200.

*Blade size*.—Grows to 14 cm long and 12 cm wide.

*Venation*.—Palmate.

*Lobing/division*.—7 shallow palmate lobes.

*Margins*.—Crenate, slightly undulate.

*Apex*.—Mucronulate.

*Base*.—Cordate, strongly overlapping and often spiraling in.

*Surface texture*.—Glandular-puberulent on both sides.

*Leaf rugosity*.—Absent.

*Petiole description*.—Grows to 19 cm long and 3.5 mm wide, glandular hairs, Greyed Purple 187A.

*Leaf color*.—New leaves; top side closest to Greyed Purple N186D with veins Greyed Purple N186A, bottom side between Greyed Purple 187A and Greyed Purple 187B with veins Greyed Purple 187A, mature leaves; top side closest to Purple N79B, veil closest to Blue Green 124D with veins Violet Blue N92A, bottom side between Greyed Purple N186C and Greyed Purple N186D with veins Greyed Purple 187D.

Inflorescence:

*Size*.—Grows to 10.5 cm wide and 25.5 cm long.

*Type*.—Thyrse, strong, upright.

*Number of thyrse*.—About 17.

*Number of flowers per thyrse*.—About 120.

*Peduncle*.—Grows to 34.5 cm long and 3 mm wide at base, glandular hairs, Greyed Purple 187A.

*Pedicel*.—Grows to 4 mm long, 0.5 mm in diameter, with glandular hairs, Greyed Purple 187A.

*Bloom period*.—Late May to late October in Canby, Oreg.

Flower bud:

*Size*.—5 mm wide and 7 mm long.

*Description*.—Glandular puberulent, ovoid, down facing.

*Color*.—Greyed Purple 187A at the base blending to Greyed Purple 187C in the middle and Red Purple 62D at tip.

Flower:

*Type*.—Perfect.

*Shape*.—Campanulate.

*Lastingness*.—30 to 45 days.

*Attitude*.—Down and side-facing.

*Size*.—7 mm long and 4.5 mm wide.

*Corolla description*.—5 petals, each 2.5 mm long and 1 mm wide at base for 0.5 mm, expanding to 2 mm wide near tip for 2 mm, spatulate, margins entire, tip acute, glandular-puberulent on outside, glabrous on inside, outside White N155A with vertical streak through the center, 0.5 mm long, Greyed Purple 186B, inside White NN155C.

*Calyx description*.—Campanulate, 4 mm long and 3 mm wide, with 5 lobes with narrow sinuses divided ½ way to the base, each 2 mm wide and 2.5 mm long, oblong in shape, back side glandular-puberulent with glandular hairs (Greyed Purple 187A), glabrous inside, tip obtuse, margin entire, inside White NN155C, tinted Red Purple 62D on back side, strongest at base.

*Stamen description*.—5 in number, filaments 1.5 mm long, White NN155C, anthers 0.5 mm long, Greyed Orange 167B, pollen none seen.

*Pistil description*.—1, 2-beaked, 8 mm long and 2 mm wide, White 155D overall, ovary 4 mm long and 2 mm wide, style 4 mm long, stigma bulbous in shape, 0.5 mm in diameter, closest to White 155C.

*Fragrance*.—None.

*Lastingness*.—Each thyrse blooms for about 3 weeks on the plant.

Fruit and seed: None.

Pest and disease tolerance: The new cultivar is typical to the genus. No known resistances to pests or diseases. No problems have been found in Canby, Oreg.

I claim:

1. A new and distinct *Heuchera* plant as herein illustrated and described.

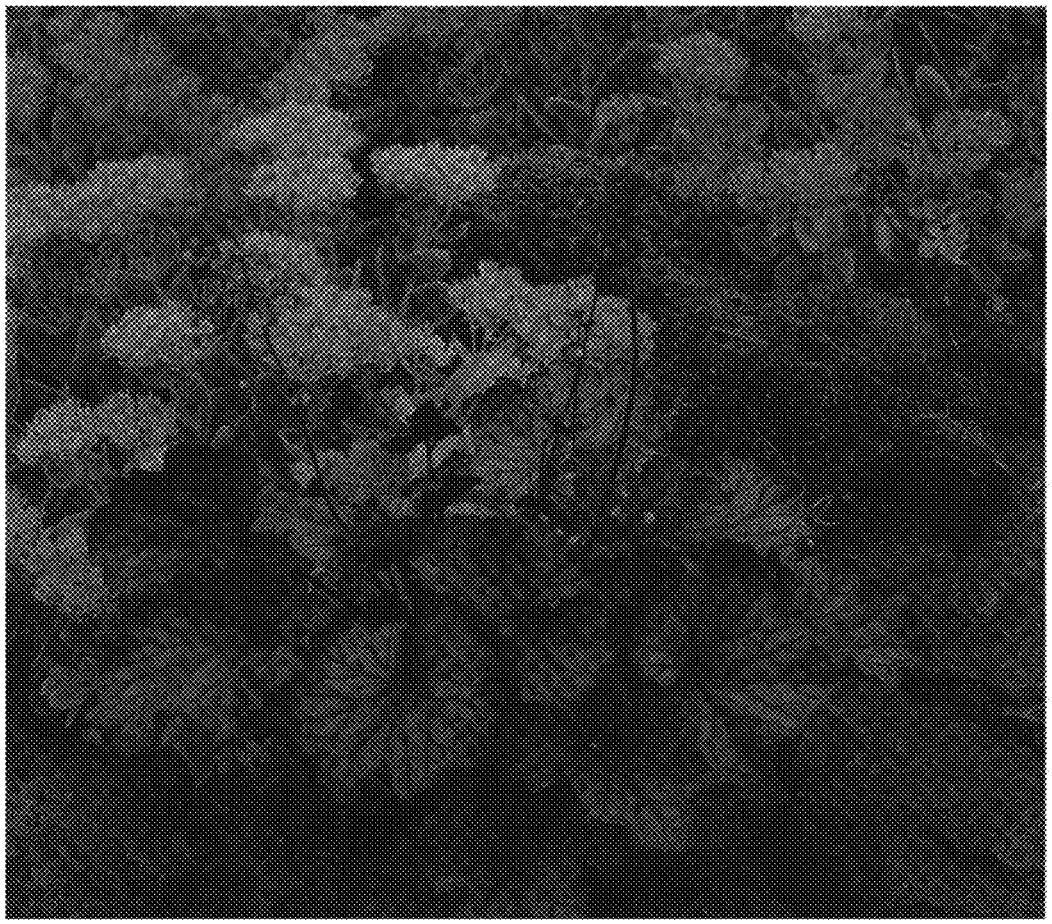

* * * * *